(12) United States Patent
Luo et al.

(10) Patent No.: US 8,263,021 B2
(45) Date of Patent: Sep. 11, 2012

(54) ROTATING MECHANISM FOR SOLID-SOLID DIRECT-HEATING REACTION DISC

(75) Inventors: Guochao Luo, Shenzhen (CN); Qisong Liu, Shenzhen (CN); Ping Tian, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 963 days.

(21) Appl. No.: 11/977,499

(22) Filed: Oct. 24, 2007

(65) Prior Publication Data

US 2008/0099192 A1     May 1, 2008

(30) Foreign Application Priority Data

Oct. 26, 2006 (CN) .................. 2006 2 0015438 U

(51) Int. Cl.
*G01N 33/00* (2006.01)
(52) U.S. Cl. .................. 422/500; 422/560
(58) Field of Classification Search .............. 422/63–66, 422/500, 560; 494/16, 18, 23, 46, 83
See application file for complete search history.

(56) References Cited

U.S. PATENT DOCUMENTS

| | | | | |
|---|---|---|---|---|
| 3,314,132 | A | * | 4/1967 | Van Dorn .................. 29/622 |
| 4,261,526 | A | * | 4/1981 | Roj .................. 242/365.4 |
| 5,111,635 | A | * | 5/1992 | Neber .................. 53/334 |
| 5,562,823 | A | * | 10/1996 | Reeves .................. 210/243 |
| 2004/0051496 | A1 | * | 3/2004 | Archer et al. .................. 318/825 |
| 2007/0104614 | A1 | | 5/2007 | Wang et al. |

FOREIGN PATENT DOCUMENTS

| | | |
|---|---|---|
| CN | 2807259 Y | 8/2006 |
| CN | 2847298 Y | 12/2006 |
| CN | 1963527 A | 5/2007 |
| WO | 9609548 | 3/1996 |

OTHER PUBLICATIONS

Chinese International Search Report dated Aug. 8, 2007 for Chinese Patent Application 200620015438.8.
English Abstract for CN1963527 (A).
English Abstract for CN2807259Y.
English Abstract for CN2847298Y.
Ma Bokun et al. "Coupling Practice Between Automatic Biochemical Analyzer and Computer" Medical Equipment Journal, 1995, pp. 30-32 (with English Abstract).
Jiang Ying "Using of Computers with Automatic Biochemical Analyzers and its Recent Developments" Information of Medical Equipment, 1994, pp. 17-19 (with English Abstract).

* cited by examiner

*Primary Examiner* — Sam P Siefke
(74) *Attorney, Agent, or Firm* — Vista IP Law Group, LLP

(57) ABSTRACT

The present invention discloses a rotating mechanism for rotationally driving a solid-solid direct-heating reaction disc, comprising a fixed hollow shaft, a rotating sleeve assembly and a signal commutator, wherein the fixed hollow shaft is fixed, the rotating sleeve assembly rotatably surrounds the fixed hollow shaft, the reaction disc is supported by the rotating sleeve assembly so as to rotate along with the rotating sleeve assembly, and the signal commutator has a stationary end fixed to the fixed hollow shaft and a moving end co-rotating with the rotating sleeve assembly. By the rotating mechanism, the signal commutator is hold, and signal input and output between the moving end and the stationary end can be achieved.

11 Claims, 2 Drawing Sheets

ROTATING MECHANISM FOR SOLID-SOLID DIRECT-HEATING REACTION DISC

CROSS-REFERENCE TO RELATED APPLICATION

Figure 1:
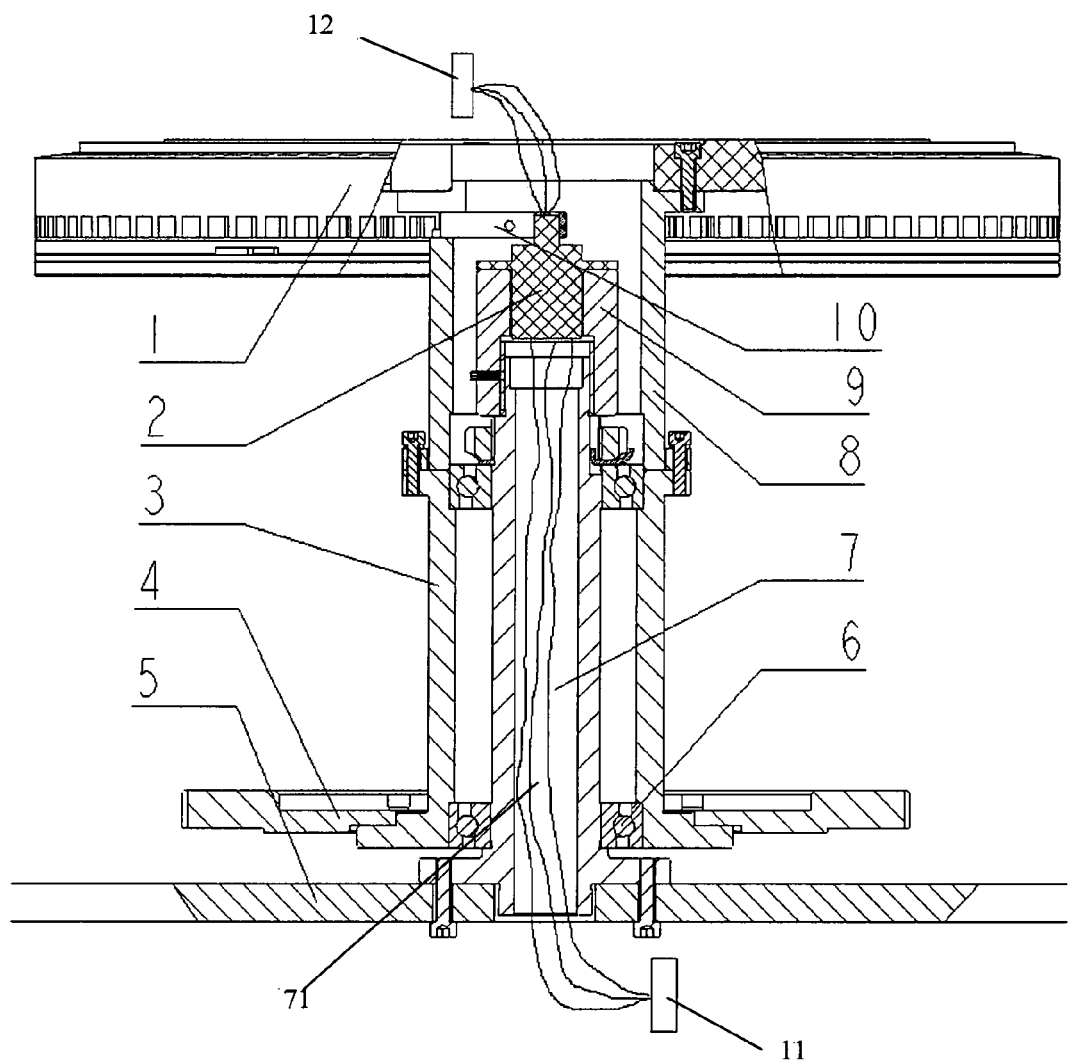

This application claims priority to Chinese Patent Application No. 200620015438.8, filed on Oct. 26, 2006.

TECHNICAL FIELD

The present invention relates to the field of automatic biochemical analyzing equipments, especially to a rotating mechanism for driving a solid-solid direct-heating reaction disc of a biochemical analyzing equipment.

BACKGROUND ART

In the present mechanisms for driving solid-solid direct-heating reaction discs, a difficulty consists in the input and output of the signals of the heaters and the temperature sensors provided in a rotated reaction disc body. To carry out the input and output of the signals, two ways are generally adopted. In the first way, the reaction disc only functions to support and hold reaction cups, and a thermostat system is individually designed, such as in the temperature control system of the known AU400 reaction disc. On the other hand, in the second way, to improve the structural integrity, a reaction cup carrying and holding system and a temperature control system are integrated into a moving reaction disc. However, it is more difficult in the second way to input and output signals to and from the reaction disc.

In this specification, the term "solid-solid direct-heating" refers to heating directly by the heat transferred between two solid objects which are contacted with each other.

SUMMARY OF INVENTION

An object of the present invention is to overcome the above shortages existed in the prior art by providing a rotating mechanism for solid-solid direct-heating reaction disc which can carry out signal input and output between a rotating reaction disc and a fixed frame.

To achieve this object, the present invention, in its one aspect, provides a rotating mechanism for rotationally driving a solid-solid direct-heating reaction disc, comprising a fixed hollow shaft, a rotating sleeve assembly and a signal commutator, wherein the fixed hollow shaft is fixed into position, the rotating sleeve assembly rotatably surrounds the fixed hollow shaft, the reaction disc is supported by the rotating sleeve assembly so as to rotate along with the rotating sleeve assembly, and the signal commutator has a stationary end fixed to the fixed hollow shaft and a moving end co-rotating with the rotating sleeve assembly.

According to an embodiment of the present invention, preferably, the signal commutator is mounted to the top end of the fixed hollow shaft via an intermediate sleeve which is engaged with the fixed hollow shaft by screw threads.

According to another embodiment of the present invention, preferably, a driven member is mounted to the moving end of the signal commutator, and a notched portion is formed through the rotating sleeve assembly in a position corresponding to the driven member, with the driven member extending into the rotating path of the notched portion, such that, when the rotating sleeve assembly is rotated, the notched portion abuts against the driven member to drive the driven member and the moving end of the signal commutator to rotate.

According to another embodiment of the present invention, preferably, the rotating sleeve assembly comprises a first rotating sleeve and a second rotating sleeve coaxially and fixedly connected to each other, the fixed hollow shaft is fitted in the first rotating sleeve by bearings, the bottom end of the second rotating sleeve is fixed to the top end of the first rotating sleeve, the top of the second rotating sleeve is fixed to the reaction disc, and the notched portion is provided in the second rotating sleeve.

According to another embodiment of the present invention, preferably, a belt pulley is mounted to the bottom end of the rotating sleeve assembly for driving it to rotate.

The present invention can thus obtain an advantage over the prior art. Specifically, by providing the signal commutator for transfer data between a stator (the frame) and a rotor (the reaction disc), with the stationary end of the signal commutator being fixed and the moving end of it being movable (rotatable) together with the rotating sleeve assembly, when the rotating sleeve assembly is rotated, the moving end of the signal commutator follows this rotation, and thus dynamic signal input and output between the moving end and the stationary end are achieved in a simple way.

BRIEF INTRODUCTION TO THE DRAWINGS

Figure 2:
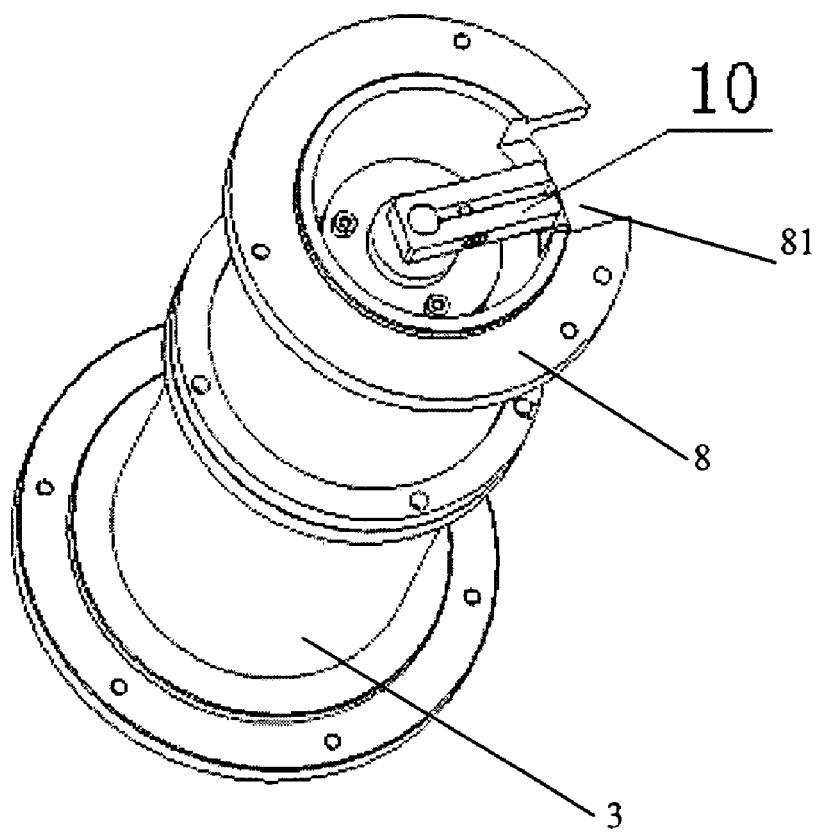

The present invention will be described in details with reference to the drawings in which:

FIG. 1 is a sectional view of a rotating mechanism for solid-solid direct-heating reaction disc of an embodiment of the present invention, with the reaction disc mounted, and FIG. 2 is a perspective view of the rotating mechanism for solid-solid direct-heating reaction disc of the embodiment of the present invention, with the reaction disc removed.

DETAILED DESCRIPTION OF THE PREFERRED EMBODIMENTS

Referring to FIGS. 1 and 2, an embodiment of the rotating mechanism of the present invention for rotationally driving a solid-solid direct-heating reaction disc 1 comprises a frame 5, a signal commutator 2, a fixed hollow shaft 7, a first -rotating sleeve 3 and a second rotating sleeve 8. Electric components, such as electric heaters, sensors and temperature control switches, are mounted to the reaction disc 1. The electric components are provided with signal transfer and power supply (input) functions via wirings which rotate along with the reaction disc 1. The frame 5 is fixed. The signal commutator 2 is a known means, which is commercially available, for transferring data between a stator and a rotor. Thus the signal commutator 2 can transfer the power supply signals for the heaters and the output signals of the sensors between the reaction disc (rotor) and the frame (stator). The signal commutator 2 has a stationary end (or fixed end) and a moving end (or movable end).

The fixed hollow shaft 7 is fixed to the frame 5 by fasteners such as screws, with a cavity chamber 71 formed through the fixed hollow shaft 7 around the center of the latter in an axial direction. The first rotating sleeve 3 surrounds the fixed hollow shaft 7 and is rotatable around the fixed hollow shaft 7 via bearings 6. An inner ring of each bearing 6 is tightly fitted on the fixed hollow shaft 7, and an outer ring of each bearing 6 is tightly nested in the inner wall of the first rotating sleeve 3. A timing belt pulley 4 is tightly fitted to the outer wall of the rotating sleeve 3 and is driven by a motor via a timing belt.

The second rotating sleeve 8 is a tube like member having an axial cavity chamber there through, the top end of which being fixed to the reaction disc 1 by fasteners such as screws, and the bottom end of which is fixed to the top end of the first rotating sleeve 3 by fasteners such as screws. The first rotating sleeve 3 and the second rotating sleeve 8 are thus fixed to each other coaxially to form a rotating sleeve assembly. The rotating sleeve assembly is also coaxial with the fixed hollow shaft 7 (i.e., the first rotating sleeve, the second rotating sleeve and the fixed hollow shaft are coaxial with each other). The stationary end of the signal commutator 2 is mounted to the top end of the fixed hollow shaft 7 via an intermediate sleeve 9 so as to be kept stationary. Preferably, the intermediate sleeve 9 is connected with the top end of the fixed hollow shaft 7 through screw threads, thus the height of the intermediate sleeve 9 in the axial direction of the fixed hollow shaft is adjustable. A driven member 10, such as a lever, is mounted to the moving end of the signal commutator 2, and a notched portion 81 is formed through the second rotating sleeve 8 in a position corresponding to the driven member 10. The driven member 10 extends into the rotating path of the notched portion 81, such that, when the second rotating sleeve 8 is rotated, the notched portion 81 drives the moving end of the signal commutator 2 to rotate by means of the driven member 10, so as to achieve the co-rotating of the signal commutator and the rotating sleeve assembly. Wirings led out from the stationary end of the signal commutator 2 extend through the cavity chamber of the fixed hollow shaft and are connected to a first PCB 11, and wirings led out from the moving end are connected to a second PCB 12 on the reaction disc.

According to the above structure of the embodiments of the present invention, the driven member 10 extends into the rotating path of the notched portion 81 of the second rotating sleeve, thus when the timing belt pulley 4 is driven by the motor via the belt to rotate, the notched portion 81 will abut against and push the driven member 10, so as to drive the driven member 10 and the moving end of-the signal commutator 2 to rotate. As a result, the first rotating sleeve 3, -the second rotating sleeve 8 and the reaction disc 1 rotate synchronizely, and the wirings of the moving end of the signal commutator rotate along with them to achieve the input and output of the signals.

The present invention is described with reference to its preferred embodiments which are not intended to restrict the scope of the present invention. A skilled in the art will readily recognize that modifications and changes can be made to the embodiments without departing from the spirit of the present invention, and accordingly all these modifications and changes may be regarded as falling within the scope of the present invention.

What is claimed is:
1. A rotating mechanism for rotationally driving a direct-heating reaction disc, comprising;
   a fixed hollow shaft;
   a rotating sleeve assembly; and
   a signal commutator, wherein
      the fixed hollow shaft is fixed and is disposed in the rotating sleeve assembly,
      the signal commutator is disposed inside the rotating sleeve assembly and has a stationary end fixedly attached to the fixed hollow shaft and a moving end rotating with the rotating sleeve assembly,
      a driven member is mounted to the moving end of the signal commutator, and a notched portion is formed through the rotating sleeve assembly in a position corresponding to the driven member, with the driven member extending into a rotating path of the notched portion, such that when the rotating sleeve assembly is rotated, the notched portion abuts against the driven member to drive the driven member and the moving end of the signal commutator to rotate, and
      the rotating sleeve assembly comprises a first rotating sleeve and a second rotating sleeve fixedly connected to each other, in which the fixed hollow shaft is fitted in the first rotating sleeve by one or more bearings, a bottom end of the second rotating sleeve is fixed to a top end of the first rotating sleeve, a top end of the second rotating sleeve is fixed to a reaction disc, and the notched portion is provided in the second rotating sleeve.

2. The rotating mechanism of claim 1, wherein the signal commutator is mounted to a top end of the fixed hollow shaft via an intermediate sleeve which is attached to the fixed hollow shaft by one or more fasteners.

3. The rotating mechanism of claim 1, wherein a belt pulley is mounted to a bottom end of the rotating sleeve assembly to drive the rotating sleeve assembly to rotate.

4. The rotating mechanism of claim 1, wherein the rotating sleeve assembly is to rotate about an axis of the fixed hollow shaft.

5. The rotating mechanism of claim 1, wherein the rotating sleeve assembly comprises a supporting mechanism to which the reaction disc is attached, and the supporting mechanism is to drive the reaction disc.

6. The rotating mechanism of claim 1, wherein the rotating sleeve assembly comprises a first component feature that engages a driven component fixedly attached to the moving end of the signal commutator to drive the moving end of the signal commutator.

7. The rotating mechanism of claim 1, further comprising:
   a frame to which the fixed hollow shaft is fixedly attached, in which the frame is to act as a stator for the signal commutator.

8. The rotating mechanism of claim 1, further comprising:
   a reaction disc fixedly attached to the rotating sleeve assembly, in which the reaction disc is to act as a rotor for the signal commutator.

9. The rotating mechanism of claim 1, further comprising:
   at least one wire with a first end and a second end, in which
      the first end of the at least one wire is operatively connected to the moving end of the signal commutator, and
      the second end of the at least one wire is operatively connected to a printed circuit board.

10. The rotating mechanism of claim 1, further comprising:
   a timing belt pulley that is operatively attached to the rotating sleeve assembly to transfer motor output for driving the rotating sleeve assembly.

11. The rotating mechanism of claim 1, further comprising:
   an adjustable sleeve to which the stationary end of the signal commutator is attached, in which
      the adjustable sleeve further comprises a first component feature that is to adjust a position of the signal commutator inside the rotation sleeve assembly.

\* \* \* \* \*